(12) United States Patent
Vanderwalle

(10) Patent No.: US 7,250,055 B1
(45) Date of Patent: Jul. 31, 2007

(54) METHOD AND APPARATUS FOR CEMENT DELIVERING BUTTRESS PIN

(75) Inventor: Mark V Vanderwalle, Pierceton, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 575 days.

(21) Appl. No.: 10/649,441

(22) Filed: Aug. 26, 2003

(51) Int. Cl.
*A61B 17/58* (2006.01)

(52) U.S. Cl. .............................. 606/92; 606/69; 606/72

(58) Field of Classification Search ................. 606/69, 606/70, 71, 72, 73, 92, 93, 94, 86; 411/393
See application file for complete search history.

(56) References Cited

U.S. PATENT DOCUMENTS

| | | | |
|---|---|---|---|
| 126,366 A | 4/1872 | Wills | |
| 837,767 A | 12/1906 | Aims | |
| 2,242,003 A | 5/1941 | Lorenzo | |
| 2,526,959 A | 10/1950 | Lorenzo | |
| 2,631,584 A * | 3/1953 | Purificato | 606/68 |
| 3,051,169 A | 8/1962 | Grath | |
| 3,240,379 A | 3/1966 | Bremer et al. | |
| 3,379,019 A | 4/1968 | Williams | |
| 3,741,205 A * | 6/1973 | Markolf et al. | 606/61 |
| 3,897,713 A | 8/1975 | Gugle | |
| 3,907,442 A | 9/1975 | Reid | |
| 3,987,499 A | 10/1976 | Scharbach et al. | |
| 4,044,512 A | 8/1977 | Fischer et al. | |
| 4,065,817 A | 1/1978 | Branemark et al. | |
| 4,098,166 A | 7/1978 | Lang | |
| 4,431,416 A | 2/1984 | Niznick | |
| 4,488,875 A | 12/1984 | Niznick | |
| 4,494,535 A | 1/1985 | Haig | |
| 4,645,453 A | 2/1987 | Niznick | |
| 4,653,487 A | 3/1987 | Maale | |
| 4,653,489 A | 3/1987 | Tronzo | |
| 4,712,957 A | 12/1987 | Edwards et al. | |
| 4,758,161 A | 7/1988 | Niznick | |
| 4,760,844 A | 8/1988 | Kyle | |
| 4,772,261 A | 9/1988 | Von Hoff et al. | |
| 4,787,882 A | 11/1988 | Claren | |
| 4,790,297 A | 12/1988 | Luque | |
| 4,860,513 A | 8/1989 | Whitman | |
| 4,893,974 A | 1/1990 | Fischer et al. | |
| 4,960,381 A | 10/1990 | Niznick | |
| 4,993,900 A | 2/1991 | Hugel et al. | |
| 5,030,095 A | 7/1991 | Niznick | |
| 5,047,030 A | 9/1991 | Draenert | |
| 5,061,181 A | 10/1991 | Niznick | |

(Continued)

FOREIGN PATENT DOCUMENTS

DE WO 01/12088 A1 2/2001

(Continued)

*Primary Examiner*—Eduardo C. Robert
*Assistant Examiner*—Nicholas Woodall
(74) *Attorney, Agent, or Firm*—Harness, Dickey & Pierce, PLC

(57) ABSTRACT

An implant assembly including a main implant and a secondary implant to fix the main implant in a relative position. The secondary implant being passable into a unprepared bone structure to securely fix the main implant in place. The secondary implant including a conduit to flow a flowable material that is able to securely interconnect the secondary implant with the bone structure.

12 Claims, 2 Drawing Sheets

U.S. PATENT DOCUMENTS

| | | |
|---|---|---|
| 5,062,800 A | 11/1991 | Niznick |
| 5,071,350 A | 12/1991 | Niznick |
| 5,076,788 A | 12/1991 | Niznick |
| RE33,796 E | 1/1992 | Niznick |
| 5,078,607 A | 1/1992 | Niznick |
| 5,098,435 A | 3/1992 | Stednitz et al. |
| 5,129,901 A | 7/1992 | Decoste |
| 5,143,498 A | 9/1992 | Whitman |
| 5,145,301 A | 9/1992 | Yamamoto |
| 5,192,282 A | 3/1993 | Draenert |
| 5,209,805 A | 5/1993 | Spraggins |
| 5,214,987 A | 6/1993 | Fenton, Sr. |
| 5,249,899 A | 10/1993 | Wilson |
| 5,253,965 A | 10/1993 | Angel |
| 5,281,140 A | 1/1994 | Niznick |
| 5,334,024 A | 8/1994 | Niznick |
| 5,338,197 A | 8/1994 | Kwan |
| 5,427,527 A | 6/1995 | Niznick et al. |
| 5,433,606 A | 7/1995 | Niznick et al. |
| 5,483,781 A | 1/1996 | Ernst et al. |
| 5,484,442 A | 1/1996 | Melker et al. |
| 5,531,748 A | 7/1996 | de la Caffiniere |
| 5,545,228 A | 8/1996 | Kambin |
| 5,569,251 A | 10/1996 | Baker et al. |
| 5,571,017 A | 11/1996 | Niznick |
| 5,575,650 A | 11/1996 | Niznick et al. |
| 5,580,352 A | 12/1996 | Sekel |
| 5,593,407 A | 1/1997 | Reis |
| 5,601,559 A | 2/1997 | Melker et al. |
| 5,622,500 A | 4/1997 | Niznick |
| 5,628,752 A | 5/1997 | Asnis et al. |
| 5,665,087 A | 9/1997 | Huebner |
| 5,725,581 A | 3/1998 | Branemark |
| 5,733,083 A | 3/1998 | Heminger |
| 5,743,912 A | 4/1998 | Lahille et al. |
| 5,788,702 A | 8/1998 | Draenert |
| 5,800,407 A | 9/1998 | Eldor |
| 5,871,484 A | 2/1999 | Spievack et al. |
| 5,885,041 A | 3/1999 | Giannuzzi et al. |
| 5,885,079 A | 3/1999 | Niznick |
| 5,893,850 A | 4/1999 | Cachia |
| 5,941,911 A | 8/1999 | Buechel |
| 5,944,721 A * | 8/1999 | Huebner ................ 606/73 |
| 5,989,028 A | 11/1999 | Niznick |
| 6,004,327 A | 12/1999 | Asnis et al. |
| 6,048,204 A | 4/2000 | Klardie et al. |
| 6,048,343 A | 4/2000 | Mathis et al. |
| 6,210,376 B1 | 4/2001 | Grayson |
| 6,214,012 B1 | 4/2001 | Karpman et al. |
| 6,240,696 B1 | 6/2001 | Ludwig et al. |
| 6,244,867 B1 | 6/2001 | Aravena et al. |
| 6,287,117 B1 | 9/2001 | Niznick |
| 6,302,885 B1 * | 10/2001 | Essiger ................ 606/72 |
| 6,517,579 B1 | 2/2003 | Paulos et al. |
| 6,565,572 B2 * | 5/2003 | Chappius ................ 606/73 |
| 6,613,053 B1 | 9/2003 | Collins et al. |
| 6,629,977 B1 | 10/2003 | Wolf |
| 6,679,890 B2 * | 1/2004 | Margulies et al. ........... 606/94 |
| 6,755,835 B2 * | 6/2004 | Schultheiss et al. ......... 606/73 |
| 2001/0021852 A1 | 9/2001 | Chappius |
| 2002/0042615 A1 | 4/2002 | Graf et al. |
| 2003/0083662 A1 * | 5/2003 | Middleton ................ 606/72 |
| 2003/0191530 A1 | 10/2003 | Sklar |

FOREIGN PATENT DOCUMENTS

| | | |
|---|---|---|
| EP | 0490417 A1 | 11/1991 |
| JP | 07-051292 | 2/1995 |
| JP | 10-211213 | 8/1998 |
| WO | WO 200117447 A * | 3/2001 |
| WO | WO 200132068 A2 * | 5/2001 |

* cited by examiner

METHOD AND APPARATUS FOR CEMENT DELIVERING BUTTRESS PIN

FIELD

The present disclosure relates generally to orthopedic implants, and particularly to buttress pins for fixation of various orthopedic implants.

BACKGROUND

Orthopedic procedures to repair the bone structures of an anatomy, such as the human anatomy, generally require fixing grafts or implants to a bone structure. The fixation of a first or primary implant to a bone structure often requires a second implant or implant portion to engage the bone structure to fix the primary implant in place. Therefore, the secondary implant must be able to engage both the bone structure and the primary implant to ensure a proper fixation and stabilization of the bone structure for healing.

When the bone portion to which the secondary implant is affixed is a strong and healthy bone, fixation of a secondary implant is generally problem free. Nevertheless, injury to bone portions are generally more prevalent with already weakened or otherwise damaged bones. Therefore, the purchase of the secondary implant into the bone portion is generally more problematic. The secondary implant may strip the bone portion into which it is implanted or loosen over time due to degradation of the bone portion.

Although purchase of a secondary implant into a bone portion can be increased by increasing, for example, the depth of the thread of a screw or including bone engaging portions on the secondary implant, the purchase of the secondary implant can still be weakened over time due to further degradation of the bone. In addition, the interior of a weakened bone can already include gaps and pores that are larger than a healthy bone thus further reducing the purchase of the secondary implant into the bone portion.

Providing a system or implant that can increase purchase in a weakened bone portion is therefore desirable. Moreover, it is desirable to provide such an implant without requiring multiple portions to be implanted into the bone portion. It is desired to provide an implant that can be implanted into the bone portion to securely hold a primary implant without requiring numerous surgical procedures or a plurality of revision procedures for a single implant procedure. Moreover, it is desired to provide an implant that can securely fix a primary implant to a bone portion, that is substantially weakened due to disease, using a substantially strong and fast fixation method.

SUMMARY

The following disclosure and appended claims relate to a buttress pin for fixation of an implant to a bone portion. The buttress pin includes a bore or cannula through which a bone cement slurry may flow. In addition, an aperture extends between the bore or cannula and an exterior of the pin. Thus, the bone cement may pass from the interior of the pin to the exterior to increase fixation and purchase of the buttress pin with the selected bone portion. Therefore, after or during the inserting of the buttress pin into the bone portion, the bone cement slurry can be passed through the bore apertures such that it will harden between the bone portion and the buttress pin to increase fixation.

The buttress pin may be substantially without threads throughout its length or shaft. Although various structures may be included, such as detents for the apertures, to increase interaction between the bone cement and the buttress pin, the buttress pin may be otherwise smooth. Nevertheless, threads may be positioned at the proximal end of the buttress pin to engage the primary implant, such as a bone plate, to increase interaction and fixation of the bone plate with the buttress pin. Therefore, a buttress pin can be provided that can securely engage weak bone portions and also securely engage a bone plate to ensure substantial fixation of a bone plate to a selected bone portion.

According to a first embodiment, an implant system to repair at least a bone portion is described. The implant system includes a primary implant to be positioned relative to the bone portion and a secondary implant operable to engage both the primary implant and the bone portion. The secondary implant includes a distal portion adapted to engage the bone portion and a proximal portion adapted to substantially engage the primary implant during and after the distal portion engages the bone portion. The secondary implant also defines a bore extending through the distal portion and the proximal portion and an aperture extending from the bore to an exterior of the secondary implant. The bore and the aperture substantially define a conduit through the secondary implant.

According to an alternative embodiment a pin implant for fixing a second implant relative to a selected bone portion is described. The pin implant includes a second implant engaging section defined by a proximal portion including a second implant engaging structure. The pin implant also includes a distal bone engaging section extending from the second implant engaging section. A bore is also defined by the second implant section and the distal bone engaging section through which a flowable material is able to flow. An aperture is defined by at least one of the second implant engaging section and the distal bone engaging section. The distal bone engaging section is able to be impacted into the bone portion. A flowable material is able to flow through the bore and the aperture to interconnect the bone engaging section and the bone portion.

According to a further alternative embodiment is described a method of fixing a first implant relative to a bone portion with a second implant. A first implant is positioned relative to the selected bone portion in a primary procedure. A second implant is passed relative to a selected portion of the first implant. A conduit is provided through the second implant to direct a flow of a flowable material through the second implant to assist in fixation of the second implant. Also, a flowable material is flowed through the second implant at a selected time to interconnect the second implant with the selected bone portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following description relates generally to implantation of bone plates, wherein the bone plate includes an aperture, it will be understood that the following description may be applied in various other applications. For example, the buttress pin may be used to hold any appropriate implant to any appropriate selected portion of the body, such as to increase fixation of a hip implant or other implants. Also, it will be understood that a bone plate may be positioned relative to any appropriate bone portion. Although the following description relates generally to a bone plate positioned relative to a long bone, such as a femur, bone plates may be formed in various sizes to be fixed at any appropriate bone portion. Therefore, the bone plate may also be fixed relative to a tibia, humerus, or any other appropriate bone portion. It will be further understood that the fixation implants may be any appropriate length, diameter, shape, or mass. The size of the fixation implant may depend upon the bone into which it is implanted, the size of the patient into which it is implanted, the degree of degradation of the bone portion, or other various factors.

Figure 1:
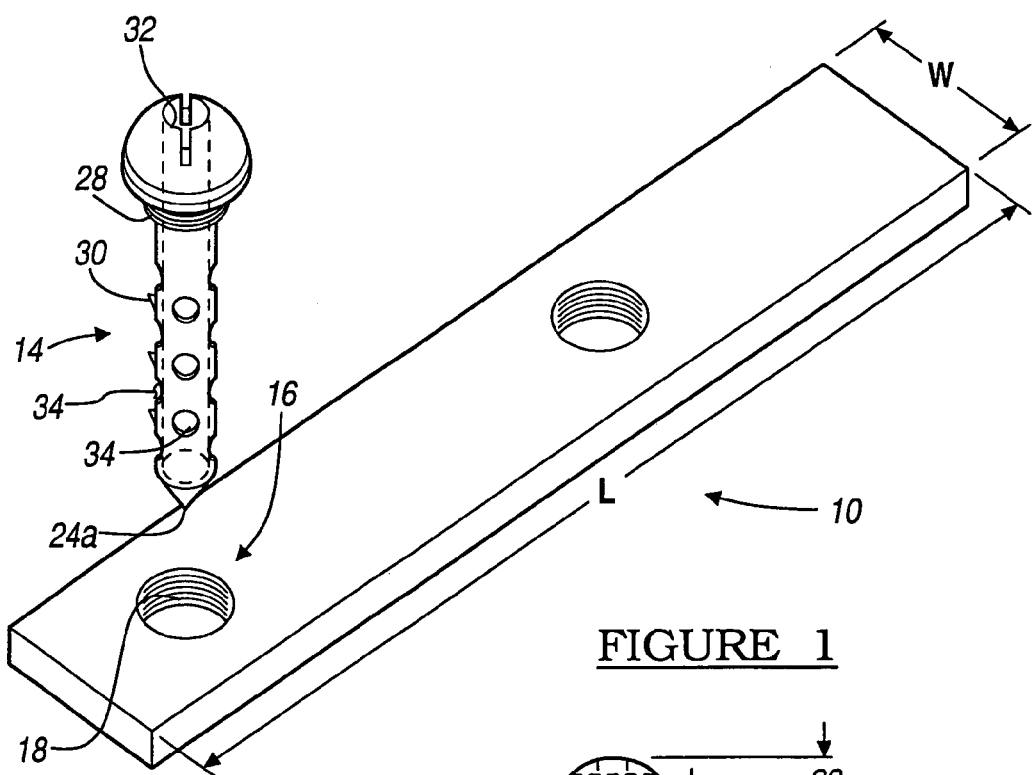
FIG. 1 is an exploded perspective view of an implant system according to a first embodiment.

With reference to FIG. 1, an implant assembly 10 generally includes a bone plate or primary implant 12 and a buttress pin or secondary implant 14. The bone plate 12 can be used for any appropriate surgical procedure such as to fix two portions of a broken bone or to increase stability of a weak or injured bone. The buttress pin 14 fixes the bone plate 12 relative to the bone portion to which the bone plate 12 is implanted. As described herein, the buttress pin 14 may be inserted through the bone plate or relative to the bone plate according to a plurality of methods.

The bone plate 12 can be formed of any appropriate shape, and is exemplary illustrated as a rectangle including a length L greater than a width W. It will be understood that the bone plate 12 may also be substantially square, circular, or include various profile shapes such as being rounded or angled. Nevertheless, the bone plate 12 generally includes at least one bore 16 formed through the bone plate 12. The bore 16 is adapted to receive a fixation device, such as the buttress pin 14. Generally, the bore 16 is formed in any appropriate design to increase or ensure fixation of the bone plate 12 relative to a bone portion. As illustrated here, a plurality of the bores 16 are formed substantially along a central axis of the rectangular bone plate 12.

The bone plate 12 can be formed of any appropriate material. Generally, the bone plate, 12 is formed of a biocompatible metal such as titanium, cobalt chromium alloys or stainless steel. Nevertheless, the bone plate 12 may be formed of other appropriate biocompatible materials such as polymers or ceramics. It will be understood that the material of the bone plate 12 is not substantially required to be any particular material, but only be appropriate for fixation of the bone portion.

The buttress pin 14 generally includes a shank or shaft portion 20 and a head or driving portion 22. The shank portion 20 includes a substantially elongated portion comprising the distal end of the shaft 20. In addition, the distal or body portion 24 generally defines a bone or an anatomical engaging portion. Extending above or proximally from the body portion 24 of the shaft 20 is a threaded or bone plate engaging portion 26. The bone plate engaging portion 26 generally defines a thread 28 that is able to engage the internal threads 18 of the bore 16. In this way, the buttress pin 14 is able to securely engage the bone plate 12.

The bone engaging portion 24 may be substantially smooth to allow for easy engagement of the buttress pin 14 into the anatomical portion. The body portion 24, however, may also define a selected geometrical shape, such as a triangle, a square, or any other appropriate shape. In addition, the body portion 14, may include barbs or anti-pullout portions 30. The barbs 30 can further engage the bone during and after implantation of the buttress pin 14 into the bone.

The head portion 22 generally includes a size greater than the diameter of the bore 16 formed in the bone plate 12. Therefore the head 22 can engage the bone plate 12 to securely hold the bone plate 12 to the bone portion. The head 12 can be formed of any appropriate geometry, but generally provided to allow for implantation of the buttress pin 14 into the bone portion. Generally, the buttress pin 14 is passed, such as through driving, pushing, or sliding the bone portion. The head portion 22 may be formed for easy engagement of a hammer or mallet to drive the buttress pin 14 into the bone portion. Alternatively, less force may be necessary and the head portion 22 may simply provide a means for a user to engage the buttress pin 14 to press it through the bone plate 12 into the bone portion. The bone plate 12 may also define a countersink to receive the head portion 22 to form a substantially smooth surface upon implantation.

Extending through the buttress pin 14 is an internal bore 32. The bore 32 may extend substantially through the buttress pin 14 or terminate at any appropriate point therein. Therefore, the buttress pin 14 may either be cannulated or only include the internal bore 32. Formed in or through the body portion 24, generally near a distal end 24a is an aperture 34. Also, a plurality of the aperture 34 may be provided. The apertures 34 extend from an exterior of the body portion 24 through to the bore 32 formed in the interior of the buttress pin 14. The apertures 34 allow for material which is transmitted through the bore 32 to exit the bore 32 to a position nearer the buttress pin 14 within the bone portion, as described further herein.

The buttress pin 14 can also be formed of any appropriate biologically compatible material. For example the buttress pin may be formed of appropriate biocompatible metals, such as titanium, cobalt chromium alloys, or stainless steel. The buttress pin 14 may also be formed of other appropriate materials, such as polymers or ceramics. Nevertheless, the buttress pin 14 generally is strong enough to substantially hold the bone plate 12 relative to the selected bone portion for an appropriate period of time. For example, the buttress pin 14 and the bone plate 12 may be formed of a bioabsorbable polymer which will absorb into the body and substantially disappear over a selected period of time. In this way, fixation with the implant system 10 is not permanent, but only operable to allow for substantial healing of the selected bone portion.

Figure 2:
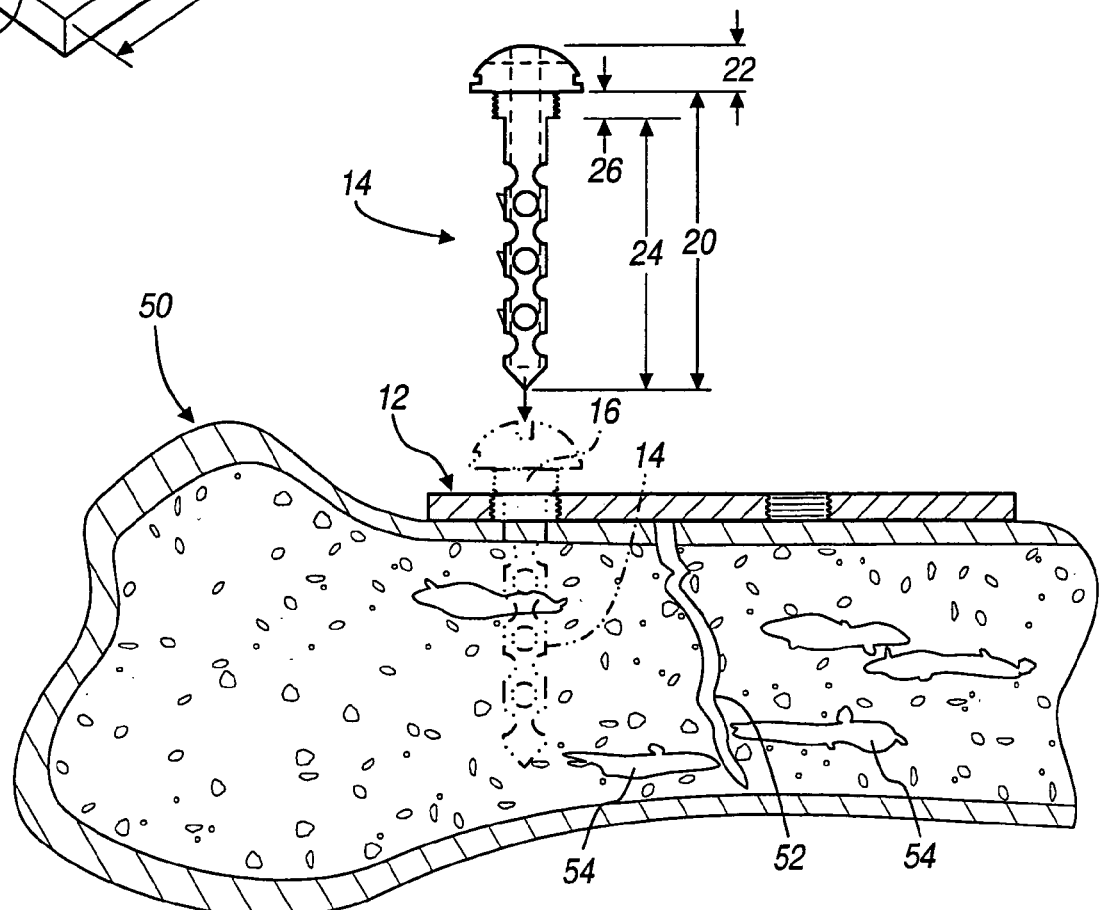
FIG. 2 is an implanted view of the implant system according to an embodiment.
Figure 3:
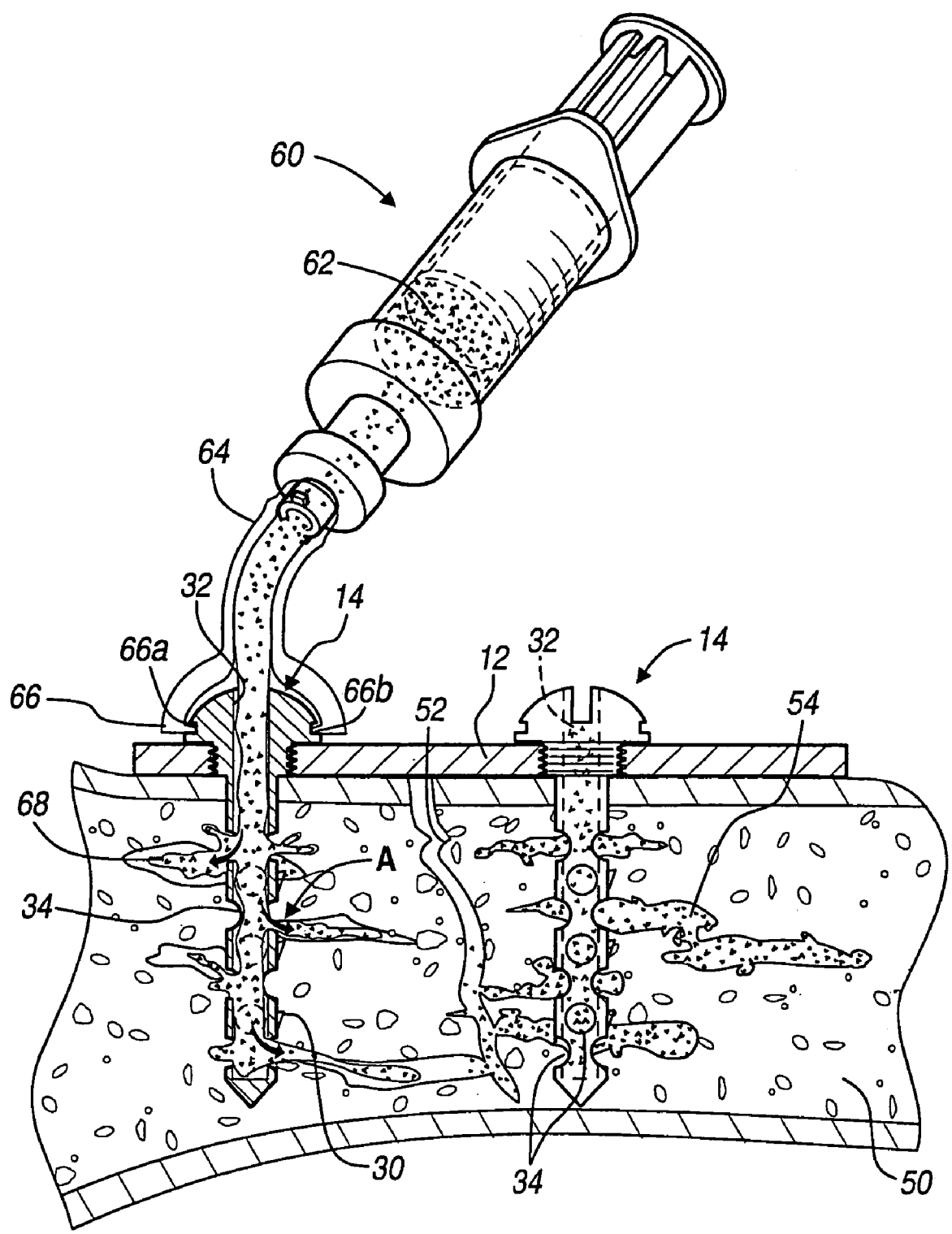
FIG. 3 is a detailed view of the implant system implanted relative to a bone portion.

With reference to FIGS. 2–3, an exemplary method of implanting the implant system 10 is illustrated. It will be understood, that the following discussion is merely exemplary and not limiting relative to the appended claims. That is, any appropriate method may be used to implant the implant system 10, including the bone plate 12 and the buttress pin 14, and the following is merely one appropriate method.

With particular reference to FIG. 2, a bone portion 50 for implantation is selected. The bone portion 50 may include a fracture 52 or any other defect 54 which is to be repaired. For example, the bone portion 50 may also include a plurality of pores or voids 54 which weaken the bone portion 50 that are desired to be reinforced or strengthened.

Once the bone portion 50 is selected, an appropriate implant, such as the bone plate 12 can be selected to be positioned relative the bone portion 50. Appropriate procedures will be understood to be taken to allow for positioning of the bone plate 12 relative to the bone structure 50. One knowledgeable in the art will understand that various incisions may be required through the dermis of the patient and other soft tissues to gain access to the bone portion 50. The particulars of these procedures are not, therefore, necessary to be described in detail here, but will be understood to have occurred to allow access to the bone portion 50.

After the appropriate surgical preparation procedures have been performed, the bone plate 12 is positioned relative to the bone portion 50. The bone plate 12 generally spans any fractures 52 and any of the weakened portions 54 that desire to be strengthened. Therefore, the bone plate 12 can be selected to be any appropriate length required to span the various repairable portions of the bone structure 50. After the bone plate 12 is positioned relative to the bone 50 in the appropriate orientation, fixation members are provided to fix the bone plate 12 relative to the bone 50. It will be understood that before the permanent or final fixation members are used to fix the bone plate 12 relative to the bone 50, temporary fixation members may be used to hold the bone plate 12 in the selected orientation to ensure that it does not move during the final implant procedure. Nevertheless, the buttress pin 14 may be provided to be passed into the bone 50 through the bone plate 12.

The buttress pin 14 may be passed through the bone plate 12 and into the bone 50. The passing or insertion of the buttress pin through the bone plate 12 may be through any appropriate method. For example, a bore may be formed in the bone portion 50 relative to one of the selected bores 16 formed by the bone plate 12 and the buttress pin 14 simply pushed through the selected bore 16 into the bore formed in the bone portion 50. The bone cement, as described herein, would provide the majority of the purchase between the buttress pin 14 and the bone portion 50. Alternatively, the buttress pin 14 may be pushed into a bore that is formed of the bone portion 50 relative to the selected bore 16 of the bone plate 12 for at least an initial friction fit. Also, the buttress pin 14 may be driven, such as with a force produced by a mallet or a hammer, into the bone portion 50 that is unprepared with a bore or other aperture. Therefore, the selected bore 16 of the bone plate 12 may be used to guide the buttress pin 14 into the bone portion 50 and the buttress pin 14 provide at least an initial purchase in the bone through the movement of the bone into which the buttress pin 14 is driven. Although the following discussion relates generally to driving the buttress pin 14 through the bone plate 12 into the bone portion 50, it will be understood that any appropriate method may be used to pass the buttress pin 14 into the bone 50.

The buttress pin 14 may be driven through one of the selected bores 16 into the bone 50. Any appropriate tool can be used to drive the buttress pin 14 into the bone portion 50 such as a hammer or mallet. Generally, the buttress pin 14 is driven through the bone plate 12 until the threads 28 of the buttress pin 14 begin to engage the threads 18 of the bore 16. That is, the buttress pin 14 is not driven through the internal threads 18 of the bore 16 so as to damage the internal threads 18. Therefore, after the buttress pin 14 is driven the appropriate distance, a tool may be used to torque the buttress pin 14 to engage the complimentary internal threads 18 to pull the buttress pin 14 through the threads 18 of the bone plate 12. Any appropriate tool may be used to drive the buttress pin 14 into the threaded portion of the bone plate 12 to securely fix the buttress pin 14 to the plate 12.

It will also be understood that the thread 28 of the buttress pin 14 may be replaced with any other appropriate structure. For example, the bore 16 and a plate engaging portion of the buttress pin 14 may be formed as complimentary tapers such as a Morse taper fit. Therefore, connection of the Morse taper will securely engage the bone plate 12 with the buttress pin 14. Alternatively, the buttress pin 14 or the bone plate 12 may deform the other to create a substantially strong interference fit. Therefore, it will be understood that the threads 28 of the buttress pin 14 and the threads 18 of the bore 16 are not limiting of the structures or methods that may interconnect the buttress pin 14 and the bone plate 12.

With particular reference to FIG. 3, the buttress pin 14 has securely engaged the bone plate 12 to preliminarily fix the bone plate 12 to the bone 50. After the buttress pin 14 has been driven through the bone plate 12, wherein the threads 28 of the buttress pin 14 engage the internal threads 18 of the bore 16, a supplementary fixation element may be provided. Generally, a bone cement slurry may be passed through the bore 32 of the buttress pin 14 and extruded through the apertures 34 of the buttress pin 14 to further engage the bone 50.

Any appropriate device may be used to allow the bone cement to be passed through the bore 32, such as a syringe 60. The syringe 60 can include a selected amount of a bone cement 62 to be provided through the bore 32. An appropriate conduit 64 can be provided to communicate the bone cement 62 from the syringe 60 to the bore 32. An appropriate fixation device 66 is used to ensure a seal between the conduit 64 and the buttress pin 14. For example, and not intended to be limiting, the fixation device 66 may include a ring portion 66A that is adapted to engage an annular depression 66B in the screw 14. Therefore, there is a substantial locking seal between the conduit 64 and the internal bore 32 so that under pressure the bone cement 62 travels through the buttress pin 14 to form the mantle 68. It will be understood that any other appropriate connection device may be used such as a clamp or threaded device.

Nevertheless, the interconnection or engaging member allows the material flowing from the syringe 60 will enter the bore 32 of the buttress pin 14 and exit in the direction of arrows A from the apertures 34. Therefore, the bone cement 62 can be provided relative to the buttress pin 14 through the bore 32 and the apertures 34 of the buttress pin 14. In this way, the bone cement slurry 62 can form a mantle 68 around the buttress pin 14.

The bone cement 62 hardens into a solid mass after a selected curing time to form the mantle 68. The bone cement mantle 68 provides fixation between the buttress pin 14 and the bone 50. The mantle 68 engages various porous portions of the bone 50 and further engages the apertures 34 and any appropriate structures formed on the buttress pin 14, such as barbs 30, to ensure a substantial fixation of the buttress pin 14 and the bone 50. Therefore, rather than relying solely on the longevity and strength of the bone near the buttress pin 14, the bone cement mantle 68 is provided to ensure a larger area of fixation between the buttress pin 14 and the bone 50. It will be understood that the bone cement mantle 68 can obtain or take on any appropriate shape depending upon the porosity and nature of the bone into which the buttress pin 14 is implanted. Nevertheless, after the bone cement mantle

68 has cured, it is substantially immobile, but includes various structures that resist pull-out of the buttress pin 14.

Therefore, the bore 32 and the apertures 34 of the buttress pin 14 allow for delivery of a bone cement slurry 62 to an area near the buttress pin 14 without attempting to first implant a bone cement slurry. In addition, the buttress pin 14 can be implanted without first forming a bore in the bone 50. This allows for greater retention of the natural bone that is still present in the bone portion 50 without the removal of the amount of the bone due to a bore formed to receive the buttress pin 14. Rather, the buttress pin 14 can be driven into unprepared bone due to the design of the buttress pin 14. Only after implantation of the buttress pin 14 is the bone cement slurry 62 provided to increase fixation of the buttress pin 14 to the bone 50. Although the buttress pin 14 may be passed into unprepared bone 50, it will be understood that the bone 50 may also have formed therein a bore into which the buttress pin 14 may be passed. After passing the buttress pin 14 into the bone, the implantation of the bone cement may increase the purchase of the buttress pin 14 relative to the bone.

In addition, the external threads 28 provided on the buttress pin 14 provide additional fixation of the buttress pin 14 relative to the bone plate 12. Because of the engagement of the buttress pin threads 28 and the bore threads 18, the bone plate 12 is less likely to creep or weaken over its lifetime. Therefore, the positive engagement of the bone cement mantle 68 with the bone and the buttress pin threads 28 with the bore threads 18, the fixation of the bone plate 12 relative to a weakened bone 50 can be substantially strengthened. Moreover, this longevity can be achieved without weakening the bone structure 50 by the requirement of forming a bore to receive an implant.

Furthermore, the buttress pin 14 can be provided to provide the bone cement slurry 62 to a selected weakened portion of the bone structure 50 after implantation of the bone plate 12. For example, the buttress pin 14 can be used to provide bone cement slurry to the voids 54 that have formed in the bone structure 50. Therefore, a separate or distinct procedure would not be required to provide bone cement to these areas. In addition, the bone cement 62 can be provided simultaneously with fixing the bone plate 12 to the bone structure 50. The bone cement can also be provided at a time distinct from implanting the buttress pin 14.

For example, the bore 32 and the apertures 34 can be provided in the buttress pin 14 during a first or primary implant procedure. The bore 32 and the apertures 34 can be appropriately covered to preserve the passage through the buttress pin 14. Then during a revision procedure, the bone cement slurry 62 can be provided through the buttress pin 14 to various weakened portions 54 that may have formed after implantation of the bone plate 12. Therefore, the buttress pin 14 can provide a first primary fixation and then at a later revision procedure be provided with a secondary fixation, such as the bone cement 62, to fill any voids or to create a bone cement mantle around a previously implanted buttress pin 14.

Although the above discussion relates generally to providing a buttress pin 14 that is driven with a substantial amount of force into a selected bone portion 50, it will be understood, as discussed above, that any appropriate method may be used to insert the buttress pin 14 into the selected bone portion 50. The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of fixing a first implant relative to a selected bone portion with a second implant, the method comprising:
   positioning said first implant relative to the selected bone portion in a primary procedure;
   passing said second implant relative to a selected portion of said first implant;
   providing a conduit through said second implant to direct a flow of a flowable material through said second implant to assist in fixation of said second implant;
   connecting a removable connector to said second implant during a revision procedure;
   flowing the flowable material through said second implant and through said first implant during the revision procedure to interconnect said second implant with the selected bone portion; and
   wherein said connecting a removable delivery device includes connecting a ring portion of a conduit of the removable delivery device to an annular depression of the fastening device to connect the delivery device to the fastening device.

2. The method of claim 1, wherein flowing a flowable material includes flowing a bone cement slurry through the second implant such that said bone cement slurry is able to cure to substantially interconnect said second implant and the selected bone portion.

3. The method of claim 1, further comprising:
   selecting the second implant to include a conduit, said conduit includes at least a bore and an aperture defined by said second implant;
   wherein flowing a flowable material includes flowing the flowable material through said bore and said aperture;
   wherein said flowable material is able to exit the second implant through said aperture to substantially interconnect the second implant and the selected bone portion.

4. The method of claim 1, further comprising:
   interconnecting the second implant with the first implant to substantially hold the first implant relative the second implant.

5. The method of claim 4, wherein interconnecting the first implant with the second implant includes threadably engaging the second implant with the first implant.

6. The method of claim 1, wherein passing said second implant includes at least one of sliding, driving, pushing, and combinations thereof.

7. A method of fastening an implant to a bone with a fastening device, the method comprising:
   positioning the implant relative to the bone during an initial procedure;
   securing the implant to the bone with the fastening device during the initial procedure;
   connecting a removable delivery device to the fastening device during a revision procedure;
   injecting a flowable material through the fastening device and into the bone using the removable delivery device;
   detaching the removable delivery device from the fastening device; and
   wherein said connecting a removable delivery device includes connecting a ring portion of a conduit of the removable delivery device to an annular depression of the fastening device to connect the delivery device to the fastening device.

8. The method of claim 7, wherein said injecting a flowable material includes injecting bone cement.

9. The method of claim 7, wherein said securing the implant to the bone includes driving threads of the fastening device into cooperation with threads of the implant.

10. A method of fastening an implant to a bone with a fastening device, the method comprising:
- positioning the implant relative to the bone during an initial procedure;
- inserting the fastening device through a bore in the implant and into the bone to secure the implant to the bone during the initial procedure;
- connecting a removable delivery device to a head of the fastening device during a revision procedure;
- injecting a flowable material through an internal bore in the fastening device that extends from the head of the fastening device to a body portion of the fastening device, the flowable material exits the body portion through an aperture in the body portion;
- detaching the removable delivery device; and
- wherein said connecting a removable delivery device includes connecting a ring portion of a conduit of the removable delivery device to an annular depression of the head of the fastening device to connect the delivery device to the fastening device.

11. The method of claim 10, wherein injecting a flowable material includes injecting bone cement.

12. The method of claim 10, wherein said inserting the fastening device through the bore includes threadably engaging threads of the fastening device with threads of the bore.

* * * * *